United States Patent [19]

Golias

[11] 4,167,467

[45] Sep. 11, 1979

[54] CLINICAL PROCEDURE FOR MEASURING LIPOPROTEIN FREE CHOLESTEROLS

[75] Inventor: Tipton L. Golias, Beaumont, Tex.

[73] Assignee: Helena Laboratories Corporation, Beaumont, Tex.

[21] Appl. No.: 928,044

[22] Filed: Jul. 26, 1978

Related U.S. Application Data

[63] Continuation-in-part of Ser. No. 835,387, Sep. 21, 1977, Pat. No. 4,105,521.

[51] Int. Cl.² .................. G01N 27/26; G01N 33/16
[52] U.S. Cl. .................... 204/180 S; 204/180 G; 204/299 R; 424/12; 23/230 B
[58] Field of Search .......... 204/180 G, 180 S, 180 R, 204/299; 424/12; 23/230 B

[56] References Cited

U.S. PATENT DOCUMENTS

| | | | |
|---|---|---|---|
| 3,808,118 | 4/1974 | Golias | 204/299 |
| 3,873,433 | 3/1975 | Seidel et al. | 204/180 S X |
| 4,041,021 | 8/1977 | Bohn | 424/12 X |
| 4,094,759 | 6/1978 | Ruhenstroth-Bauer et al. | 204/180 G |

*Primary Examiner*—Arthur C. Prescott
*Attorney, Agent, or Firm*—Cullen, Sloman, Cantor, Grauer, Scott & Rutherford

[57] ABSTRACT

An electrophoresis method of determining the concentration of high density lipoprotein (HDL) free cholesterols in body fluids and simultaneously determining the concentration of very low density lipoprotein (VLDL) and low density lipoprotein (LDL) free cholesterols in the fluid. The method includes applying a small sample of the fluid to an electrophoresis support medium, applying a direct current across the medium, applying a developing substrate to the electrophoresed lipoproteins and quantitatively determining the concentration of each lipoprotein free cholesterol. This method does permit direct and simultaneous measurement of each lipoprotein free cholesterol fraction while eliminating precipitation of each fraction as required by the prior art.

12 Claims, No Drawings

CLINICAL PROCEDURE FOR MEASURING LIPOPROTEIN FREE CHOLESTEROLS

RELATED APPLICATION

This application is a continuation in part application of my earlier filed application for United States Patent, Ser. No. 835,387, filed Sept. 21, 1977, now U.S. Pat. No. 4,105,521.

FIELD OF THE INVENTION

The present invention relates to a clinical method of determining the concentration of lipoprotein free cholesterol fractions, particularly high density lipoprotein (HDL) free cholesterol in serum, plasma and other body fluids. My prior co-pending application discloses and claims a method of determining the density fractions of the combination of free cholesterol and cholesterol esters in a body fluid sample. It is now believed that free cholesterols, particularly the high density lipoprotein fraction, is an even better indicator or predictor of cardiovascular risk. However, a reliable and simple method of determining the high density lipoprotein fraction of free cholesterols in body fluid has not been available.

Blood serum cholesterol has been recognized for over thirty years as associated with coronary artery diseases. Medical experts have long believed that persons having elevated serum cholesterol levels are more likely to surffer myocardial infarcation (heart attack) than persons having lower levels of cholesterol. However, the correlation between cholesterol levels and coronary artery disease is not consistent and therefore the present diagnostic tests for cholesterol are considered advisory only and not a reliable indicator of the likelihood of myocardial infarcation or premature coronary artery disease.

The more recent work by the National Heart, Lung and Blood Institute of Bethesda, Md and the Framingham Heart Institute of Framingham, Mass. has suggested that one fraction of cholesterol, high density lipoprotein, is actually a "predictor of inverse cardiovascular risk". This discovery should improve our understanding of the role of cholesterol in coronary artery diseases. Further, a correlation between free cholesterol and esterified cholesterol in each lipoprotein fraction (HDL, LDL and VLDL) and cardiovascular risk may also be found. Therefore, a simple, fast and reliable test for the concentrations of lipoprotein free cholesterol fractions in body fluids is necessary.

The present clinical tests for determining the concentration of high density lipoprotein (HDL) free cholesterol in body fluid requires precipitation of the other cholesterol fractions (low density and very low density lipoproteins) and determination of the free cholesterol concentration in the supernate. Briefly, the recommended test includes adding heparin solution to the fluid sample and mixing, adding manganese chloride and mixing, chilling and drawing off the supernate. All of the free cholesterol remaining in the supernate is assumed to be high density lipoprotein free cholesterol. The cholesterol is extracted with isopropanol and the extract assayed for free cholesterol in spectrophotometers or continuous-flow analyzers.

It will be apparent that this procedure has several disadvantages. The procedure is slow and therefore expensive. Because precipitation is used, the reliability of the test is suspect. Finally, the assumption that all of the free cholesterol remaining after precipitation is high density lipoprotein has been seriously questioned. The problem with this assumption is the lack of specificity of the commonly used cations, specifically $Ca^{2+}$, $Mg^{2+}$ and $Mn^{2+}$, in the lipoprotein-heparin interaction. Further, it has been found that subclasses of high density lipoproteins can be precipitated in the presence of manganese cations. Thus, the precipitation method may not be as reliable as believed.

The method of determining the concentration of lipoprotein free cholesterol fractions of the present invention eliminates these problems and provides a simple and reliable clinical procedure.

SUMMARY OF THE INVENTION

Cholesterol occurs in blood serum in two forms, namely free cholesterol and cholesterol esters. Both forms are bound to serum proteins along with other lipids (i.e., triglycerides, phospholipids, et cetera) to form lipoproteins. These lipoproteins occur in different densities as initially determined by ultracentrifugation. The density fractions are generally referred to as high density lipoproteins (HDL) cholesterol, very low density lipoprotein (VLDL) cholesterol and low density lipoproteins (LDL) cholesterols. It will be understood that further fractions have been identified including subclasses of HDL cholesterol, however these are the principal features. As set forth above, the present method provides a simple and reliable determination of the density fractions of free cholesterol in body fluids, providing an important additional indicator for clinical testing.

Although certain proteins have been separated by electrophoresis methods, such methods have not been successful in separating smaller molecules such as cholesterol. The method of this invention takes advantage of the fact that free cholesterol is bound to serum proteins, permitting separation by electrophoresis methods. As described, the method of this invention permits simultaneous determination of the concentrations of high density lipoprotein, very low density lipoprotein and low density lipoprotein free cholesterols in body fluids such as serum, plasma, etc. The procedure is as follows.

First, a small sample of the body fluid to be tested is applied to a solid electrophoresis support media, preferably cellulose acetate. The support media will generally be in the form of a strip. Next, a direct current is applied across the support media for a predetermined time to separate the high density, very low density and low density lipoprotein cholesterols on the media. Next, a developing substrate sensitive to small concentrations of free cholesterol is applied to the electrophoresed lipoprotein free cholesterols, developing the separated lipoprotein free cholesterols on the support media, the free cholesterols appearing reddish-brown in color. Finally, the concentrations of each of the lipoprotein free cholesterols may be quantitatively determined by one or any of several methods, including direct densitometry or by eluting each fraction and measuring the concentration of each lipoprotein in the eluate.

The method of the present invention thus permits simultaneous measurement of high density lipoprotein free cholesterol, low density lipoprotein free cholesterol and very low density lipoprotein free cholesterol. The procedure is faster and less costly than the present clinical methods because the procedure of the present invention eliminates precipitation. Finally, the method of the present invention is more reproducible because the determination of the lipoprotein free cholesterol concentrations are made directly from the entire sample. Other advantages and meritorious features of the present invention will be more fully understood from the following detailed description.

DETAILED DESCRIPTION OF THE METHOD OF THIS INVENTION

The method of determining concentrations of lipoprotein free cholesterols of this invention is basically an electrophoretic determination. Thus, a small sample of the body fluid to be tested is first applied to a solid electrophoresis support media, preferably cellulose acetate. A suitable cellulose acetate support media is available in strip form from the assignee of the present invention under the trade name "Titan III". It will be understood that other support media including cellulose nitrate, agar, agarose, paper acrylamide gel, cellulose propionate, silica gel, starch gel, etc. may also be used. The fluid sample is preferably applied to the support media in a straight line, permitting accurate reading following electrophoresis. A suitable apparatus for applying the fluid sample to the support media is disclosed in U.S. Pat. No. 4,006,705.

Next, a direct electric current is applied across the media, causing separation of the lipoprotein free cholesterol fractions. Movement of the lipoprotein free cholesterols through a medium such as cellulose acetate depends upon the medium, the intensity of the electric field, the time and the character of the charged particle. In view of the fact that these variables will be constant for each lipoprotein free cholesterol fraction, the fractions are separated upon application of the electric field. It has been found that optimum separations for lipoprotein free cholesterols occur at about one hundred eighty (180) volts (DC) for about twenty minutes. It has been found that the order of separation is HDL, VLDL and LDL free cholesterol, which is the order given herein.

Following electrophoresis, a developing sensitive to small concentrations of cholesterol is applied to the electrophoresed lipoprotein cholesterol strip. In the preferred embodiment, the developing substrate is a cholesterol oxidase substrate such as available from Boehringer Mannheim Corporation, Indianapolis, Ind. The cholesterol oxidase available from Boehringer Mannheim Corporation is used to measure free cholesterol enzymatically. In the method of the present invention, the electrophoresed lipoprotein cholesterols are incubated with the cholesterol oxidase substrate for about fifteen minutes at 37° Centigrade. A suitable cholesterol oxidase substrate may have the following formulation:

Sodium cholate: 58.0 mM
4-Aminoantipyrine: 8.0 mM
Phenol: 106.0 mM
Peroxidase (horseradish): 20.0 U/mL
Cholesterol oxidase (bacterial): 0.75 U/mL
Buffer and other non-reactive ingredients.

The developing substrate may be applied to the electrophoresed free cholesterols by one of several methods, including simply soaking or submerging the support media in the reagent or, more preferably, sandwiching the support media to another support media that has been impregnated with the reagent. For example, a strip of cellulose acetate as described above may be soaked or impregnated with cholesterol oxidase reagent. A sandwich of a strip of cellulose acetate impregnated with the reagent and the electrophoresed media is then made, which is incubated as described above.

Where the developing substrate is a cholesterol oxidase reagent, the lipoprotein free cholesterols are stained a reddish-brown color and are easily visualized on the support media. Further, as described, the lipoprotein fractions have been separated during electrophoresis, permitting quantitative determination of the concentration of the high density lipoprotein, very low density lipoprotein and low density lipoprotein free cholesterols.

Quantitation may be accomplished by one of several methods. In the simplest method, the support media is scanned by a suitable instrument for measuring absorbence, such as a densitometer. Althernatively, the individual fractions may be eluted and the absorbence measured by a spectrophotometer. As will be understood by those skilled in the art, other quantitative methods may also be utilized. For example, the cholesterol oxidase reagent may be tagged with fluorescene or a radioactive isotope, such as iodine 125. Where fluorescene is used, the concentration of each fraction may be determined by a fluorescent densitometry or spectrophotometry. Where a radioactive isotope is utilized, the concentrations are determined by measuring the radioactivity of each sample using a radioisotope scanner. Additionally, where a thin sheet or strip of cellulose acetate is used for the electrophoresis support medium, the individual lipoprotein fractions may be cut out with scissors. Then, each fraction may be dissolved and the fluorescence or radioactivity of each sample measured. This provides a very accurate determination.

It will be understood by those skilled in the art that various modifications may be made to the method of determining the concentration of lipoprotein free cholesterols of this invention. Further, details of the electrophoretic method will be understood by those skilled in the art. For example, U.S. Pat. No. 4,005,434 discloses a method and apparatus for graphic densitometer display which may be used in the method of this invention.

I claim:

1. A method of simultaneously determining the concentrations of high density lipoprotein free cholesterol, very low density lipoprotein free cholesterol and low density lipoprotein free cholesterol in a sample of body fluid, comprising the steps of:
   (a) applying a small sample of said body fluid to be tested to a solid electrophoresis support media strip,
   (b) applying a direct current for a predetermined period of time to said support media until the high density, very low density and low density lipoprotein free cholesterols have separated on the media,
   (c) applying a developing substrate sensitive to small concentrations of free cholesterol to the electrophoresed lipoprotein strip, and
   (d) quantitatively determining the concentrations of high density lipoprotein, very low density lipoprotein and low density lipoprotein free cholesterols in said body fluid sample from the developed electrophoresed sample.

2. The method of determining concentrations of lipoprotein free cholesterols in a sample of body fluid defined in claim 1, wherein said developing substrate is a cholesterol oxidase substrate which is applied to said electrophoresis support media.

3. The method of determining concentrations of lipoprotein free cholesterols in a sample of body fluid defined in claim 2, wherein said cholesterol oxidase is applied to said support media by immersing the media in a fluid sample of said cholesterol oxidase reagent.

4. The method of determining concentrations of lipoprotein free cholesterols in a sample of body fluid defined in claim 2, wherein said cholesterol oxidase substrate is applied to said support media by impregnating an untreated strip of support media with fluid cholesterol oxidase reagent and applying said impregnated strip to the electrophoresed lipoprotein free cholesterols in a sandwich form and incubating the sandwiched media for a predetermined period of time.

5. The method of determining concentrations of lipoprotein free cholesterols in a sample of body fluid defined in claim 1, wherein said electrophoresis support media is cellulose acetate and said direct current is about one hundred eighty (180) volts which is applied to said support media for about twenty minutes.

6. The method of determining concentrations of lipoprotein free cholesterols in a sample of body fluid defined in claim 1, wherein the concentrations of the lipoprotein free cholesterols are quantitatively determined by a densitometer by measuring absorbance of each lipoprotein free cholesterol following application of the developing substrate.

7. The method of determining concentrations of lipoprotein free cholesterols in a sample of body fluid in claim 1, wherein said quantitative determination is made by eluting each electrophoresed fraction, including high density lipoprotein, very low density lipoprotein and low density lipoprotein free cholesterol and then quantitatively determining the concentration of each fraction.

8. The method of determining concentrations of lipoprotein free cholesterols in a sample of body fluid defined in claim 7, wherein the concentration of each fraction is determined using a spectrophotometer.

9. The method of determining concentrations of lipoprotein free cholesters in a sample of body fluid defined in claim 7, wherein said cholesterol oxidase reagent is tagged with fluorescene, including quantitatively determining the concentration of each fraction by measuring the fluorescence.

10. The method of determining concentrations of lipoprotein free cholesterols in a sample of body fluid defined in claim 7, wherein said cholesterol oxidase is tagged with a radioactive isotope, including quantitatively determining the concentration of each fraction by measuring the radioactivity of each fraction with a radioisotope counter.

11. A method of determining the concentration of high density lipoprotein free cholesterol in body fluid, comprising:
    (a) applying a small sample of said body fluid to a solid electrophoresis support media,
    (b) applying a direct current across said electrophoresis support media until the high density lipoprotein free cholesterol has separated from any remaining lipoprotein in said sample,
    (c) applying a developing substrate sensitive to high density lipoprotein free cholesterols to the separate electrophoresed high density lipoprotein free cholesterols, and
    (d) quantitatively determining the concentration of the high density lipoprotein free cholesterol present in said body fluid from said developed electrophoresed sample.

12. The method of determining the concentration of high density lipoprotein free cholesterol in a fluid sample defined in claim 11, wherein said developing substrate is a cholesterol oxidase substrate and said support media is cellulose acetate, including applying said cholesterol oxidase to the electrophoresed sample on said cellulose acetate media.

* * * * *